United States Patent [19]

Schmidt

[11] Patent Number: 5,634,932

[45] Date of Patent: Jun. 3, 1997

[54] CANTILEVER ANEURYSM CLIP SYSTEM

[75] Inventor: Ferenc J. Schmidt, Bryn Mawr, Pa.

[73] Assignee: Industrial & Scientific Designs, Ltd., Dalkey, Ireland

[21] Appl. No.: 541,485

[22] Filed: Oct. 10, 1995

[51] Int. Cl.⁶ .......................... A61B 17/08; A61B 17/04
[52] U.S. Cl. ........................................ 606/157; 606/142
[58] Field of Search ................................. 606/142, 144, 606/139, 157, 158

[56] References Cited

U.S. PATENT DOCUMENTS

| | | |
|---|---|---|
| 535,798 | 3/1895 | Hawkes . |
| 1,352,978 | 9/1920 | Lantieri et al. . |
| 3,326,217 | 6/1967 | Kerr . |
| 3,518,993 | 7/1970 | Blake . |
| 4,024,868 | 5/1977 | Williams . |
| 4,440,170 | 4/1984 | Golden et al. . |
| 4,478,219 | 10/1984 | Rozario et al. . |
| 4,527,562 | 7/1985 | Mericle . |
| 4,681,107 | 7/1987 | Kees, Jr. . |
| 4,943,298 | 7/1990 | Fujita et al. . |
| 4,966,603 | 10/1990 | Focelle et al. . |
| 5,201,746 | 4/1993 | Shichman . |
| 5,234,449 | 8/1993 | Bruker et al. . |
| 5,304,188 | 4/1994 | Marogil . |
| 5,354,306 | 10/1994 | Garvey, III et al. . |
| 5,520,701 | 5/1996 | Lerch .............................. 606/142 |

FOREIGN PATENT DOCUMENTS

| | | |
|---|---|---|
| 0178469 | 4/1986 | European Pat. Off. . |
| 0630615 A1 | 12/1994 | European Pat. Off. . |

OTHER PUBLICATIONS

Mizuho Ikakogyo Co. Catalog, pp. 2–7 (Apr., 1995).
AESCULAP (Aneurysm–Clip System) Brochure, 2 pages (1995).
AESCULAP (Forceps) Brochure, 4 pages (1995).
*Handbook of Spring Design*, p. 31 (Spring Manufacturers Institute 1981).
AESCULAP® Catalog, 2 pages (1992).
"Spring Design Data," Section 4, p. 4 (AMETEK, Inc. 1964).
European Search Report dated 19. Sep. 1994 (attached to above listed EP Publication No. 0 630 615).
Axel Perneczky, M.D. and Georg Fries, M.D., "Use of a new aneurysm clip with an inverted–spring mechanism to facilitate visual control during clip application," *J. Neurosurg*, vol. 82, pp. 898–899 (May, 1995).

*Primary Examiner*—Michael Buiz
*Assistant Examiner*—Tina T. D. Pham
*Attorney, Agent, or Firm*—Ratner & Prestia

[57] ABSTRACT

A system for clipping an aneurysm which includes an aneurysm clip and an applicator that allows improved visual control during application. The aneurysm clip has a unitary, integral, cantilever spring and a unitary, integral, rigid ring. The cantilever spring has two arms, open in the unbiased position, provides a spring force, and defines the clipping force of the aneurysm clip. The cantilever spring also includes bulges positioned on the outer surface of the arms and a bend at the ends of the arms. The rigid ring slips over the arms, is retained by the bulges, and forces the arms together. The applicator includes a first leg including a pin adapted to engage the bend of the cantilever spring of the aneurysm clip and a second leg movable relative to the first leg which includes structure for engaging the rigid ring of the aneurysm clip. A scissoring or squeezing motion of the applicator handle moves the arms to slide the rigid ring on and off the arms of the cantilever spring of the aneurysm clip.

27 Claims, 5 Drawing Sheets

CANTILEVER ANEURYSM CLIP SYSTEM

FIELD OF THE INVENTION

This invention relates generally to a cerebral aneurysm clip and, in particular, to an aneurysm clip system that improves visual control during clip application. The system includes an aneurysm clip, having a cantilever spring and a rigid ring, and an applicator.

BACKGROUND OF THE INVENTION

A cerebral aneurysm is an expansion of an artery in the brain into the form of a lump or balloon. Aneurysms are often located behind other blood vessels and at various angles. They may be difficult to reach. Moreover, access to a cerebral aneurysm is through a very small opening.

A cerebral aneurysm clip is a surgical instrument which clips the base part of a cerebral aneurysm to temporarily or permanently isolate it from the cerebral artery. For this purpose, the clip must maintain its pressure with high reliability as long as desired without injury to the wall of the blood vessel. Such injury might be caused, for example, by a shearing action of the clip arms, which results from improper alignment; improper clipping pressure; foreign material trapped in cracks and crevices formed in the clip design; surface imperfections on the clip material which can tear tissue; or the use of unsuitable materials to manufacture the clip.

Figures 1, 2:
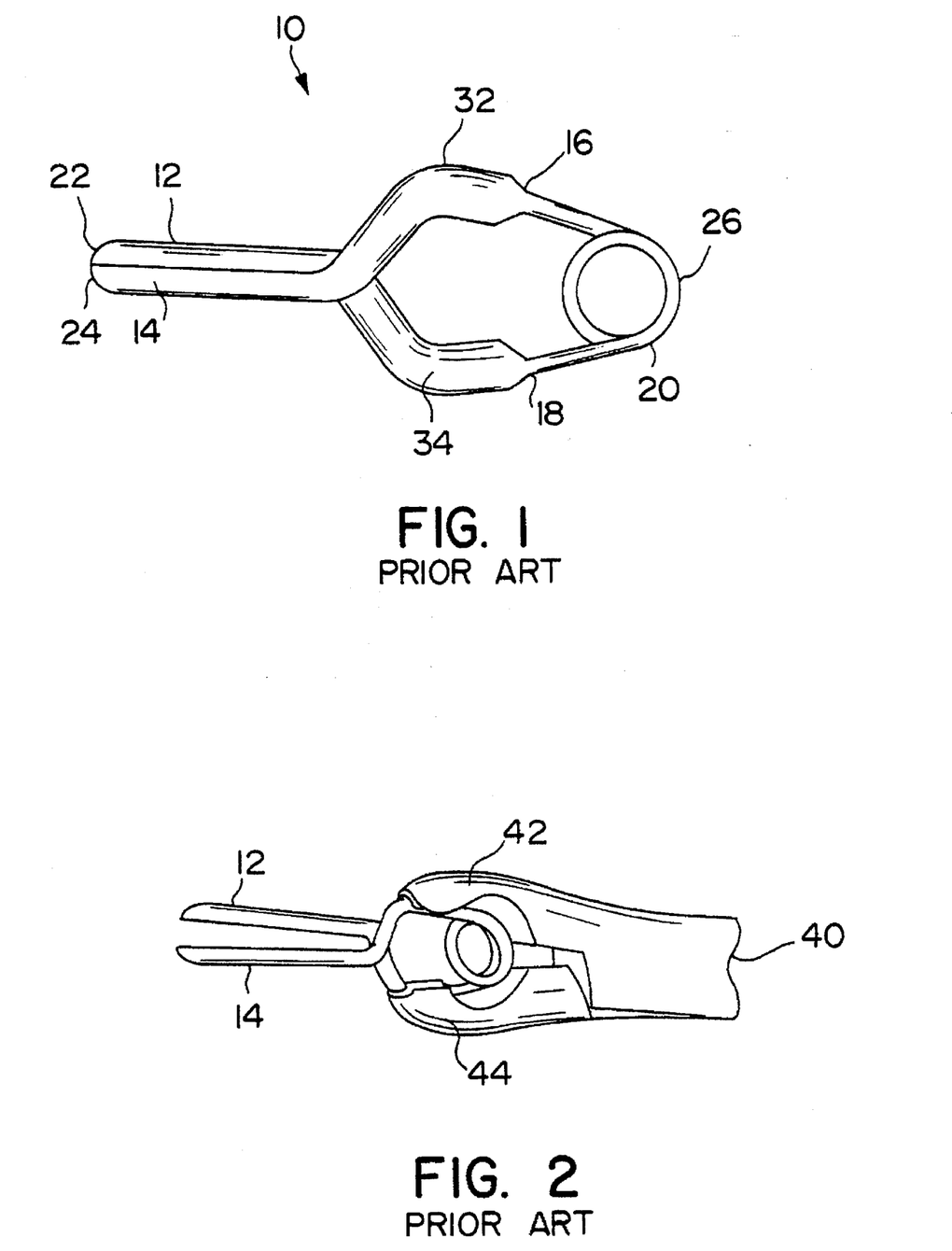
FIG. 1 illustrates a conventional aneurysm clip having a coil spring.
FIG. 2 shows how the conventional aneurysm clip illustrated in FIG. 1 is applied using a known applicator.

FIG. 1 illustrates a conventional cerebral aneurysm clip 10. Clip 10 has a pair of blades 12 and 14 which are positioned to face each other. A coil spring 20, generally called a "torsion" spring, is formed between the base ends 16 and 18 of blades 12 and 14. Typically, coil spring 20 has one-and-one-half (as shown in FIG. 1) or two-and-one half coils. The free ends 22 and 24 of blades 12 and 14 clip the aneurysm. Blades 12 and 14 are opened and closed using the base end 26 of coil spring 20 as a fulcrum. The elasticity of coil spring 20 provides clip 10 with its clipping force.

FIG. 2 shows how conventional cerebral aneurysm clip 10 is applied using an applicator 40. Applicator 40 has a pair of jaws 42 and 44 which envelop and engage the bases 32 and 34 of blades 12 and 14 of clip 10. (As shown in FIG. 2, conventional applicator 40 is larger than the clip 10 which it applies; therefore, the combination of clip 10 and applicator 40 provides a larger visual obstruction than the clip alone.) When jaws 42 and 44 are compressed, bases 32 and 34 of clip 10 pivot toward one another about base end 26 and against the force of coil spring 20. That movement opens free ends 22 and 24 of blades 12 and 14. The neurosurgeon then positions opened free ends 22 and 24 of blades 12 and 14 around the vessel to be clipped. When jaws 42 and 44 are subsequently released, bases 32 and 34 of clip 10 pivot away from one another about base end 26 under the force of coil spring 20. That movement closes free ends 22 and 24 of blades 12 and 14 and clips the aneurysm in the vessel.

Distinguish an aneurysm clip from a "clamp." Clamps use malleable materials which close like a staple, lack the flexibility of a spring component, and cannot be removed. Consequently, clamps do not allow precise tailoring of the closing forces to (1) prevent dislocation, yet (2) prevent necrosis of the tissues due to overly high pressure. The clamping force is determined by how tightly the clamp is closed, not by a pre-calibrated spring force. In addition, clamps cannot form the complex shapes into which clips must be manufactured. The clip must be applied, through a very small opening, often deep inside the brain.

When operating on a deep-seated cerebral aneurysm, the neurosurgeon's visual control of the clip application is restricted by both the clip and the clip applicator. That problem has been identified, for example, in the article by A. Perneczky, "Use of a New Aneurysm Clip with an Inverted-Spring Mechanism to Facilitate Visual Control During Clip Application," J. Neurosurg 82: 898–899 (1995). Obstruction dimensions for an aneurysm clip and applicator are typically 9 mm by 5 mm. The 9 mm dimension represents the width of the clip coil (about 7 mm) plus the approximately 1 mm applicator head on either side enveloping the clip coil (see FIG. 2). These dimensions are large when compared to cerebral arteries as small as 1 mm in diameter.

One recent development (the Perneczky clip) inverts or reverses the clip action. The applicator grips the inside of the clip and does not envelop the clip. To open the clip, the applicator is opened; the applicator is closed to close the clip. This eliminates the applicator as a source of obstruction. Because the 1 mm obstruction by the applicator on either side of the clip is eliminated, the obstruction with this clip is typically reduced to the order of 7×5 mm.

A number of different materials are used to manufacture cerebral aneurysm clips. Most conventional aneurysm clips are limited, however, to metals and metal alloys (such as stainless steel and chrome-cobalt alloy steel) because the clips incorporate coil springs and metals and their alloys provide the necessary spring force to clip tissue. Unfortunately, most metals and metal alloys interfere with important diagnostic techniques such as magnetic resonance imaging (MRI or NMR), MRA, and CT-Scanning due to image degradation (haloing, starbursts, and "Black-Hole" obscuring) caused by the magnetic characteristic and high density of the materials. An exception is titanium, which has a very low magnetic susceptibility and density; therefore, it does not interfere with MRI, MRA, or CT-scan procedures.

Furthermore, the significant magnetic susceptibility of most metals and metal alloys presents the danger that clips made of these materials will move, rotate, or become hot in the intense electro-magnetic fields created. Aneurysm clips made of non-metallic materials including plastic, ceramic, or composites—and the exceptional metal titanium—present advantages, such as minimal interference with MRI, MRA, and CT-scan diagnostic procedures. The problem of metallic materials of construction has been discussed in U.S. Pat. No. 4,943,298 issued to Fujita et al.

The cerebral aneurysm clip of the '298 patent has blades made of synthetic resins or ceramics. The synthetic material can include, for example, fluorine or methacrylic resins or thermoplastics such as polyethylene or polypropylene. Table 1 of the '298 patent summarizes applicable ceramic materials. The advantage of such materials is disclosed as the ability to make X-ray and MRI examinations without interference from the materials. The materials also provide an advantage in that they are chemically stable and harmless to a living body, as well as being corrosion resistant and durable.

The first embodiment of the '298 patent is an otherwise standard clip improved by using plastic or ceramic material of construction. This embodiment is illustrated in FIGS. 1–5 of that patent. The second embodiment is illustrated in FIGS. 6–10 of the '298 patent. The second embodiment is a hinged clip, neither closed nor open unless biased, having blades 14a, 14b or 25a, 25b which pivot about a single point. The clip has an elastic spring member which is either compressed (see FIGS. 6 and 10) or stretched (see FIGS. 7–9) to apply a closing force on the blades. The spring member can be a sleeve shown as element 27 in FIG. 9.

The '298 patent does not disclose any way to prevent the elastic spring member from slipping on the clip. Moreover, the clipping force is not developed, in the clip of the '298 patent, by any cantilever action of the blades. Rather, the clipping force is developed by elastic springs which are made of rubber or other elastomers. Finally, the '298 patent does not disclose any type of applicator. It appears, however, that the applicator must envelop the clip and impair visibility.

Some conventional clip designs require that holes be drilled, components be welded or riveted, or recesses be formed. Machining processes are often required. Such manufacturing procedures introduce microcracks, voids, and crevices into the clip. Sharp corners of recesses and microcracks yield a clip undesirable for use as a cerebral implant. Thus, drilling, welding, riveting, and machining steps should be avoided in the processes of manufacturing an aneurysm clip; otherwise, the clip produced cannot satisfy the criteria required for a desirable clip.

The aneurysm clip disclosed by Lerch in European Patent Application No. 94108657.1 is an example of a titanium clip which requires problematic machining steps during manufacture. The clip is made from two rod halves, each half having a free end, a bump, a curved area, and a foot. The free ends of the clip halves form the clip jaws. The two rods are held together by a crimp (which has an edge or shoulder) on the feet. A ring rests on the curved area of the halves before the clip is applied. Before application, the ring jaws are spread apart. A hole is drilled through the ring and a rod is inserted in the hole so that it protrudes on either side of the ring. The ring is illustrated in FIG. 3 of the application.

The principle problem with the titanium clip disclosed by Lerch is the requirement that a crimp be provided. The crimp is objectionable, first, because it is an additional component that increases the cost of the clip and must be designed and formed with precision. Titanium and its alloys are notch sensitive; therefore, they are difficult to deform without cracking. Cracks are likely to occur when the crimp of the clip is formed. In addition, the crimp has an edge or shoulder that renders the clip undesirable for use as a cerebral implant. If a more malleable metal than titanium is used to form the crimp, the advantages of titanium would be lost and the risk of other problems (such as galvanic corrosion) arises. A crimping operation is difficult to implement with other, non-metallic materials of construction such as plastics and ceramics.

Similarly, the drilling operation on the ring may introduce microcracks, voids, and crevices into the ring. The protruding rod on either side of the ring yields undesirable extensions on a clip for use as a cerebral implant. Finally, like the crimp, the protruding rod of the ring is objectionable because it is an additional component that increases the cost of the clip and must be designed and formed with precision.

The applicator used to apply the clip has a pistol-like handle, a tube moved by the handle, and a fixed locator rod inside the tube (see FIG. 1 of the application). The locator rod has a seat with jaws on its end. With the tube pulled away from the clip, the jaws of the seat on the locator rod are positioned over the edges of the crimp on the clip (see FIG. 5 of the application). The user then slides the tube over the locator rod and forces the jaws of the seat on the locator rod around the edges of the crimp so that the locator rod holds the crimp of the clip (see FIG. 6 of the application). The user continues to slide the tube over the locator rod until an uptake slot on the end of the tube engages the protruding rod on either side of the ring. Using a wheel, the tube is rotated so that the uptake slot "catches" the protruding rod. Finally, the user slides the tube until the clip is within the tube and the ring is positioned over the bumps on the clip halves. This action forces the jaws of the clip together. (See FIG. 7 of the application.)

The applicator disclosed by Lerch surrounds the clip. Therefore, the applicator is larger than the clip and restricts the view of the neurosurgeon. During application, the neurosurgeon must accomplish the additional procedural step of rotating the tube so that the uptake slot of the applicator tube catches the protruding rod of the clip ring. This introduces another inconvenient and time-consuming procedural step (requiring the use of two hands), however, and is undesirable because the uptake slot may fail to catch the clip ring unless the step is performed correctly.

To overcome the shortcomings of existing aneurysm clips, a new cantilever aneurysm clip system is provided that reduces visual obstruction. An object of the present invention is to provide an improved aneurysm clip incorporating a cantilever spring force. A further object is a design that does not require coil springs and that can be easily manufactured from almost any material, including titanium, ceramic, plastic, or composites. It is still another object of the present invention to provide an improved applicator that is positioned next to, rather than around, the aneurysm clip, to further improve visual control. Another object of the present invention is to achieve an adequate closing force using less spring material than is required by conventional coil clips; therefore, the weight of the clip is reduced.

SUMMARY OF THE INVENTION

To achieve these and other objects, and in view of its purposes, the present invention provides a system for clipping an aneurysm which includes a unitary, integral, cantilever spring; a rigid ring; and an applicator that allows improved visual control during application. The cantilever spring is open in the unbiased position. The rigidity of the material provides the spring force and defines the clipping force of the aneurysm clip. The cantilever spring further includes (i) a first arm with a first end, a free end, an outer surface, and at least one bulge positioned on the outer surface; (ii) a second arm with a first end, a free end, an outer surface, and with or without at least one bulge positioned on the outer surface; and (iii) a generally "U" or "V"-shaped bend disposed between the first end of the first arm and the first end of the second arm.

The aneurysm clip also includes a rigid ring with opposing faces adapted to slip over and completely surround the first and second arms. The ring is retained by the bulge or bulges on the first, and possibly on the second, arm. The ring presses the arms together into a closed position against the spring force, creating a cantilever spring clip rather than a coil spring clip, while preventing scissoring of the first and second arms.

The cantilever spring aneurysm clip is applied by the neurosurgeon using an applicator. The applicator of the present invention is a modified Rongeurs type and allows improved visual control during application of the cantilever spring aneurysm clip. The applicator includes a first leg having a pin adapted to engage the "U" or "V"-shaped bend of the cantilever spring of the aneurysm clip. A second leg moves relative to the first leg and includes structure for engaging the ring of the aneurysm clip to slide the ring on and off the arms of the cantilever spring. The first and second legs are positioned alongside the aneurysm clip rather than around it, thereby reducing visual obstruction. The applicator has a handle including a blade attached to each leg to move the second leg relative to the first leg.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawings, in which.

DETAILED DESCRIPTION OF THE INVENTION

As illustrated in the drawings, the clip of the present invention looks much like a "U" or "V"-shaped hair pin in its simplest embodiment. Conventional aneurysm clips are based on various coil springs which are basically similar to clothes pins. The resilient coil spring develops the closing force in such conventional clips and the spring arms are so short and stiff that their effect on the closing force is universally neglected.

In contrast, the clip of the present invention substitutes a cantilever spring force for the coil spring force of the conventional clips, thereby permitting use of a wide variety of rigid materials (e.g., titanium, plastics, ceramics, and reinforced composites) some of which do not lend themselves to forming into a spring coil. In addition, the "U" or "V"-shape can be cut out from sheets, molded, or formed using a wide variety of manufacturing techniques. The use of plastics, ceramics, and reinforced composites offers recognized advantages in many implant applications.

The closing force developed by the arms, negligible in conventional clips, is the sole closing force for the clip of the present invention. The closing force is determined by the rigidity (resistance to bending) of the material and can be calculated using beam equations—not torsional spring equations. Thus, the closing force is developed using a different principle (bending versus torsion spring) than that found in conventional devices.

Figure 3:
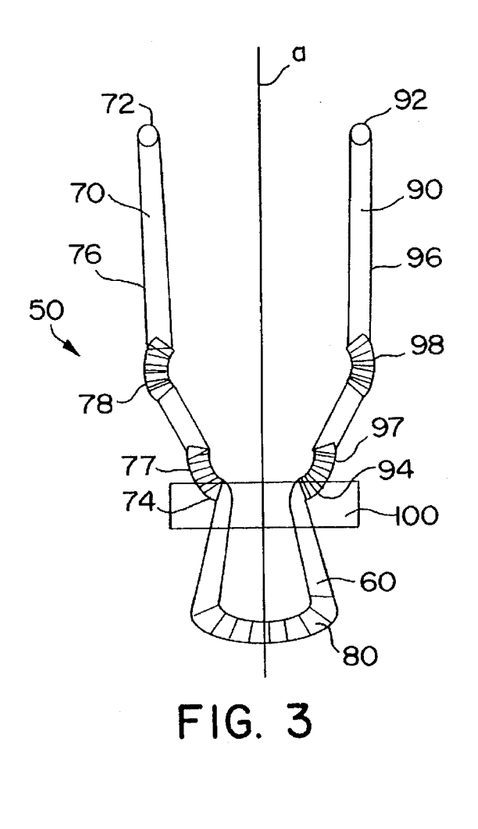
FIG. 3 depicts a first embodiment of the aneurysm clip of the present invention, including a cantilever spring and a rigid ring, in an open position.
Figure 4:
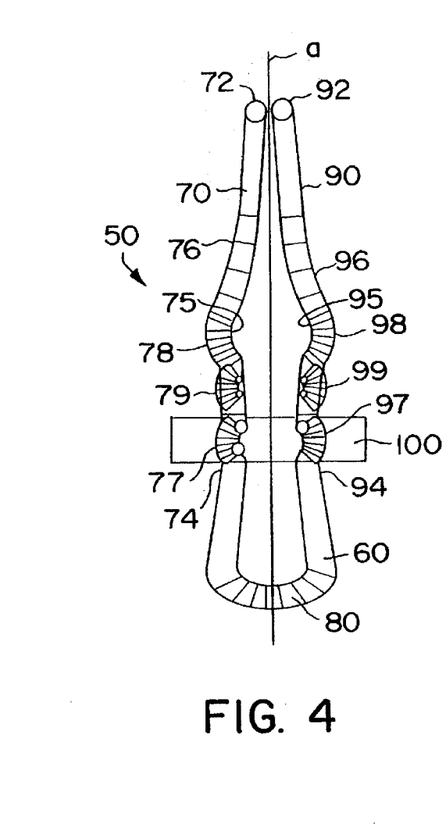
FIG. 4 shows a second (and preferred) embodiment of the aneurysm clip of the present invention, also with a cantilever spring and a rigid ring, in a partially closed position.
Figure 5:
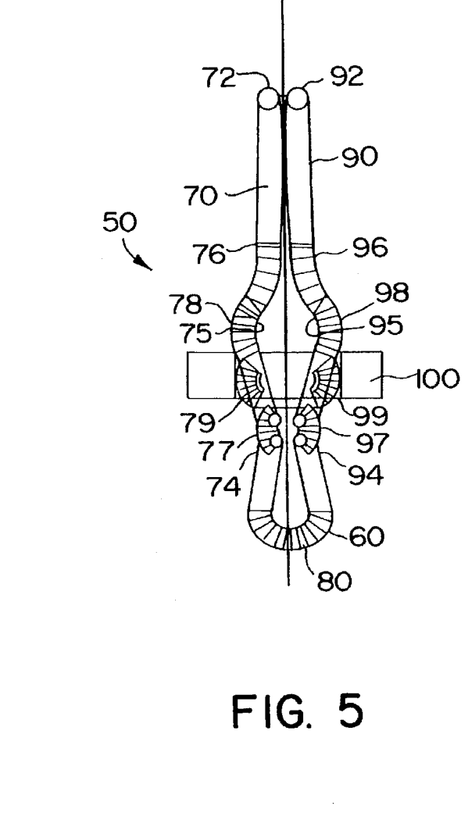
FIG. 5 illustrates the aneurysm clip shown in FIG. 4 in a fully closed position.

Referring now to the drawing, wherein like reference numerals refer to like elements throughout, FIG. 3 shows a first embodiment of the aneurysm clip 50 of the present invention disposed along longitudinal axis "a". Aneurysm clip 50 has two components: a cantilever spring 60 and a rigid ring 100. As discussed above, drilling, welding, riveting, and other machining steps should be avoided in the processes of manufacturing aneurysm clip 50. Accordingly, each component of aneurysm clip 50 of the present invention-cantilever spring 60 and rigid ring 100—is unitary and integral. FIGS. 4 and 5 illustrate a second embodiment of aneurysm clip 50 as ring 100 is applied to cantilever spring 60.

Cantilever spring 60 of aneurysm clip 50 has a first arm 70 and a second arm 90. First arm 70 has a free end 72, a first end 74, and an outer surface 76. Second arm 90 has a free end 92, a first end 94, and an outer surface 96. Cantilever spring 60 has a generally "U" or "V"-shaped bend 80 disposed between first end 74 of arm 70 and first end 94 of arm 90.

Figure 7:
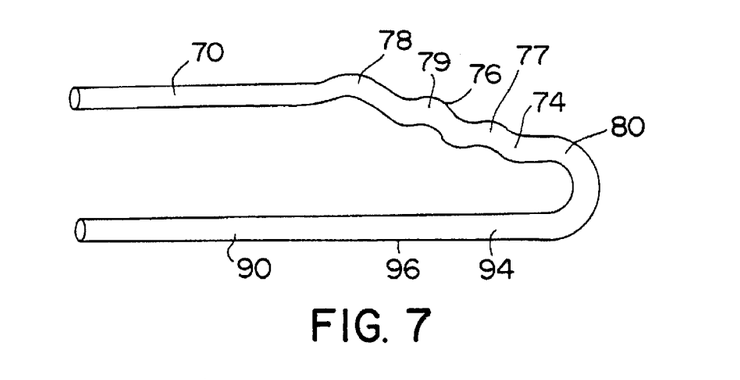
FIG. 7 shows an embodiment of the cantilever spring component without any bulges on the second arm according to the present invention.

At least one of the outer surfaces, for example outer surface 76, has a first bulge 77. In the embodiment shown in FIG. 3, outer surface 76 also has a second bulge 78. FIG. 7 shows an embodiment of cantilever spring 60 without any bulges on second arm 90. Alternatively, as shown in FIG. 3, outer surface 96 of second arm 90 also may have a first bulge 97 and a second bulge 98. The function of bulges 77, 78, 97, and 98 will be described below.

In a preferred embodiment of the invention, cantilever spring 60 has a width of approximately 4.5 mm and the length of bend 80 is approximately 4 mm. Because cantilever spring 60 avoids the need for a coil spring, cantilever spring 60 can be made of 0.5 mm thick, flat-strip material in titanium. Conventional clips require a 1 mm thickness; a thinner material would not allow formation of a coil spring having sufficient strength. Accordingly, the volumetric visual obstruction of aneurysm clip 50 is only 0.5×4.5×4.0 mm.

Figure 6A:
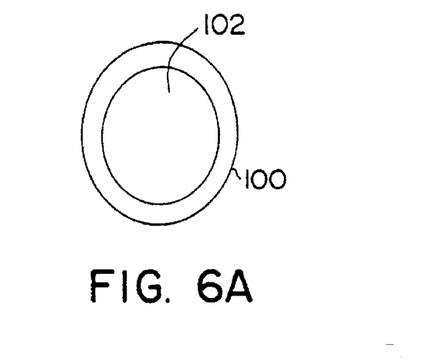
FIG. 6A is a front view of the rigid ring of the aneurysm clip according to the present invention.
Figure 6B:
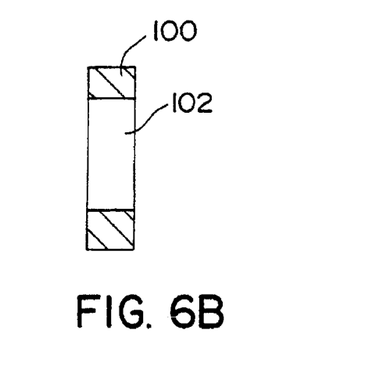
FIG. 6B is a side view of the rigid ring shown in FIG. 6A.

The second component of aneurysm clip 50 of the present invention is rigid ring 100. FIG. 6A is a front view of rigid ring 100; FIG. 6B is a side view of rigid ring 100. Cantilever spring 60 is set for application by sliding rigid ring 100 with opening 102 over arms 70 and 90 until adjacent to bend 80 as shown in FIG. 3. The outer diameter of bend 80 is larger than the inner diameter of ring 100; consequently, ring 100 cannot slide off cantilever spring 60 in the direction of bend 80.

Cantilever spring 60 is closed by sliding rigid ring 100 with opening 102 and by positioning rigid ring 100 over arms 70 and 90 to press arms 70 and 90 into a gently closed position. Rigid ring 100 is preferably made rigid and in an oval shape, as shown in FIG. 6A, to prevent sideways movement (scissoring) of first arm 70 and second arm 90 when rigid ring 100 is positioned over and around arms 70 and 90. In the preferred embodiment of the invention, rigid ring 100 has a height of about 2 mm and a maximum outside diameter of about 5 mm.

As illustrated in FIG. 3, before application of rigid ring 100 to cantilever spring 60, aneurysm clip 50 might be considered equivalent to a conventional coil spring clip— albeit with only a one-half coil turn. When unbiased and before application of rigid ring 100, cantilever spring 60 assumes an open position as shown in FIG. 3. Once applied, however, rigid ring 100 essentially pins arms 70 and 90 (immobilizing the coil spring equivalent) and transforms arms 70 and 90 of cantilever spring 60 into beams restrained at one end (i.e., into cantilever beams).

FIGS. 4 and 5 illustrate a preferred embodiment of cantilever spring 60 of aneurysm clip 50. Whereas first arm 70 and second arm 90 of cantilever spring 60 shown in FIG. 3 are each provided with only a first bulge (77 and 97, respectively) and a second bulge (78 and 98, respectively), first arm 70 and second arm 90 of preferred cantilever spring 60 shown in FIGS. 4 and 5 each have a third bulge 79 and 99, respectively. First bulges 77 and 97 prevent rigid ring 100 from sliding off arms 70 and 90 in the direction of bend 80. Second bulges 78 and 98 prevent rigid ring 100 from sliding off arms 70 and 90 in the direction of free ends 72 and 92.

During application, rigid ring 100 is placed adjacent bend 80 (see FIG. 3) and forced over first bulges 77 and 97 (see FIG. 4) until it seats between first bulges 77, 97 and second bulges 78, 98 (see FIG. 5). Typically, second bulges 78 and 98 are larger than first bulges 77 and 97. Thus, rigid ring 100 is retained between first bulges 77, 97 and second bulges 78, 98.

FIGS. 4 and 5 illustrate a preferred embodiment of cantilever spring 60 in which arms 70 and 90 each have a third bulge 79 and 99. Like first bulges 77 and 97, third bulges 79 and 99 are smaller than second bulges 78 and 98. Rigid ring 100 engages third bulges 79 and 99, when fully applied to cantilever spring 60, and third bulges 79 and 99 provide additional closing pressure. As noted above, the dimensions of aneurysm clip 50 are critical. Each of bulges 77, 78, 79, 97, 98, and 99 are about 2 mm long for a clip with a total length of about 27.5 mm.

The preferred embodiment of cantilever spring 60 illustrated in FIGS. 4 and 5 also incorporates another feature not present in the embodiment of cantilever spring 60 illustrated in FIG. 3: angles for the arms. First and second arms 70 and 90 may each be provided with an angle 75 and 95, respectively, in the proximity of third bulges 79 and 99. Angles 75 and 95 are directed inward so that arms 70 and 90 of cantilever spring 60 assume a non-parallel position having slightly converging free ends 72 and 92 when cantilever spring 60 is in its open position. Distinguish the embodiment of cantilever spring 60 shown in FIG. 3 in which free ends 72 and 92 are substantially parallel to (and may diverge away from) longitudinal axis "a" before application.

Arms 70 and 90 continue to converge during the application process (see FIG. 4). When fully applied to a vessel, however, arms 70 and 90 will assume a substantially parallel orientation (see FIG. 5). Angles 75 and 95 enhance the cantilever spring force of aneurysm clip 50 so that the clipping force of aneurysm clip 50 is equal to or greater than the clipping force generated by the coil spring of conventional clip 10. Angles 75 and 95 also reduce the risk of slippage of arms 70 and 90 from the blood vessel. Most significantly, angles 75 and 95 provide a safe upper limit to the pressure applied to a vessel by aneurysm clip 50 and reduce the danger of necrosis of the tissue due to excessive pressure.

When aneurysm clip 50 is fully applied to a vessel, arms 70 and 90 will touch (or nearly touch) in the vicinity of first bulges 77 and 97 (see FIG. 5). Accordingly, any effect of bend 80 as a "coil" in contributing to the clipping force of aneurysm clip 50 is cancelled. The clipping force of aneurysm clip 50 is defined entirely by the rigidity of the material used to construct cantilever spring 60.

A preferred embodiment of aneurysm clip 50 was constructed of titanium and tested. Aneurysm clip 50 attained a closing force of between 150–200 grams. Moreover, aneurysm clip 50 required less metal than an equivalent coil spring clip 10.

Although neither preferred nor illustrated, a single bulge may be provided on one arm of cantilever spring 60 to retain rigid ring 100. Rigid ring 100 may have a groove on its inside diameter to ride on the single bulge without danger of slippage. Alternatively, each of the arms 70 and 90 of cantilever spring 60 may be provided with a single bulge to retain rigid ring 100. Thus, various combinations of different numbers of bulges on each arm of cantilever spring 60 are possible. The preferred embodiment of cantilever spring 60 is shown in FIGS. 4 and 5, however, with each arm 70 and 90 having three bulges.

In the embodiments of the present invention discussed thus far, the spring force of cantilever spring 60 is the only spring force of aneurysm clip 50. It is sometimes necessary, however, to remove aneurysm clip 50 for various reasons. For example, the neurosurgeon may try, or "titrate," blood flow with clips of various shapes and closing force. Therefore, it may be desirable to include an additional force to ensure re-opening of aneurysm clip 50. The additional force is unnecessary for clips made from sufficiently resilient materials. It is an added safety feature, however, for materials which could develop a "set" in the closed position due to plastic flow.

Figure 8:
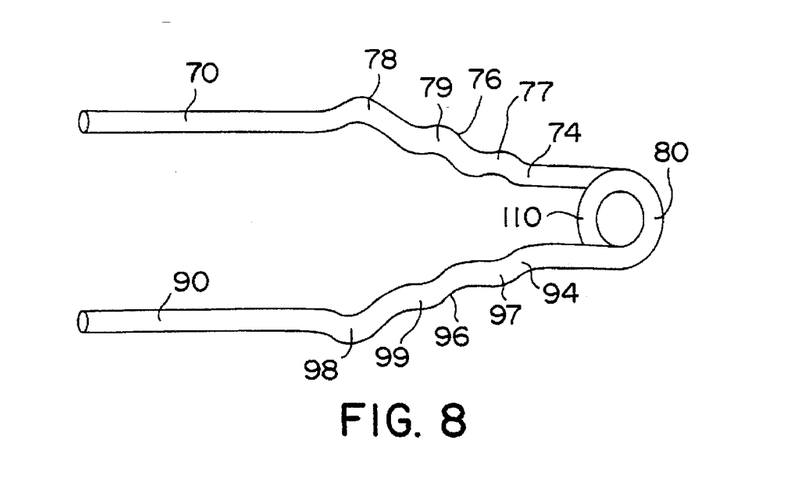
FIG. 8 is an embodiment of the aneurysm clip according to the present invention which includes a coil spring disposed in the bend of the cantilever spring component.

FIG. 8 shows an embodiment of cantilever spring 60 in which a coil spring 110 with at least one coil is positioned in the trough of bend 80 to provide additional opening force to arms 70 and 90 when rigid ring 100 is removed. In contrast to coil spring aneurysm clips, like aneurysm clip 10, the function of coil spring 110 is not to develop closing force (pressing arms 70 and 90 together); rather, the function is just the opposite—to ensure re-opening of arms 70 and 90 once rigid ring 100 is removed. Such re-opening must be made possible because the clips are removed and repositioned occasionally from cerebral arteries.

The closing force generated by coil spring 110, if one is provided, is nil or negligible. In either case, the closing force attributable to coil spring 110 can be neglected in designing aneurysm clip 50 of the present invention.

Figure 9:
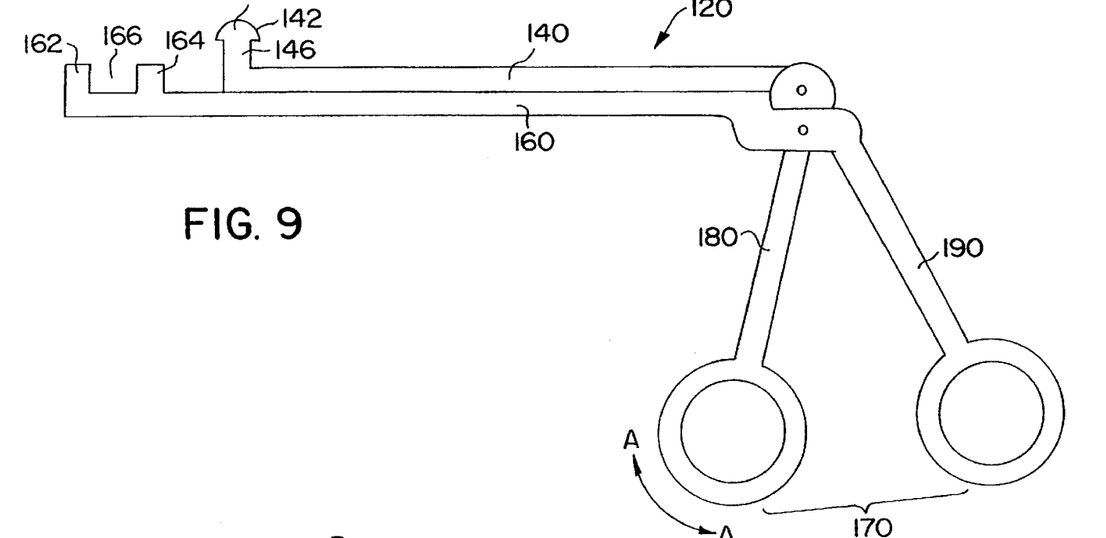
FIG. 9 is an applicator according to the present invention using a scissoring motion of the handle.

FIG. 9 shows an applicator 120 used to apply aneurysm clip 50 of the present invention. Applicator 120 is a modified "Rongeurs" type of applicator with a first leg 140 and a second leg 160. First leg 140 has a pin 142 disposed perpendicular to and near the end of first leg 140. Pin 142 engages bend 80 of cantilever spring 60 of aneurysm clip 50. Pin 142 may include a rounded head 144 with a diameter slightly larger than the diameter of the body 146 of pin 142 to prevent pin 142 from slipping out of bend 80 unless a twisting motion is applied. Second leg 160 includes structure for engaging rigid ring 100 of aneurysm clip 50. In one exemplary embodiment, such structure consists of two perpendicular projections 162 and 164 with a space 166 located between projections 162 and 164.

Figure 10:
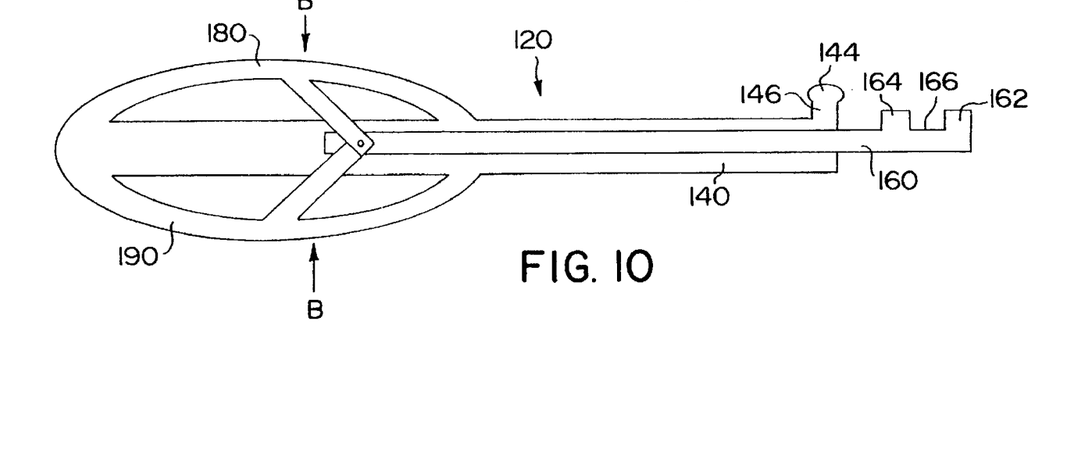
FIG. 10 is another embodiment of the applicator according to the present invention using a squeezing motion of the handle.

First leg 140 and second leg 160 are mounted so that they are movable relative, and slide parallel, to one another. Applicator 120 includes a handle 170 which has a first blade 180 mounted on first leg 140 at the end of first leg 140 opposite pin 142. Handle 170 also has a second blade 190 mounted on second leg 160 at the end of second leg 160 opposite projections 162 and 164. Handle 170 moves legs 140 and 160 relative to one another either by a scissoring motion, as shown by arrow "A" in FIG. 9, or by a squeezing motion, as shown by arrows "B" in FIG. 10, of blades 180 and 190 of handle 170.

Figure 11:
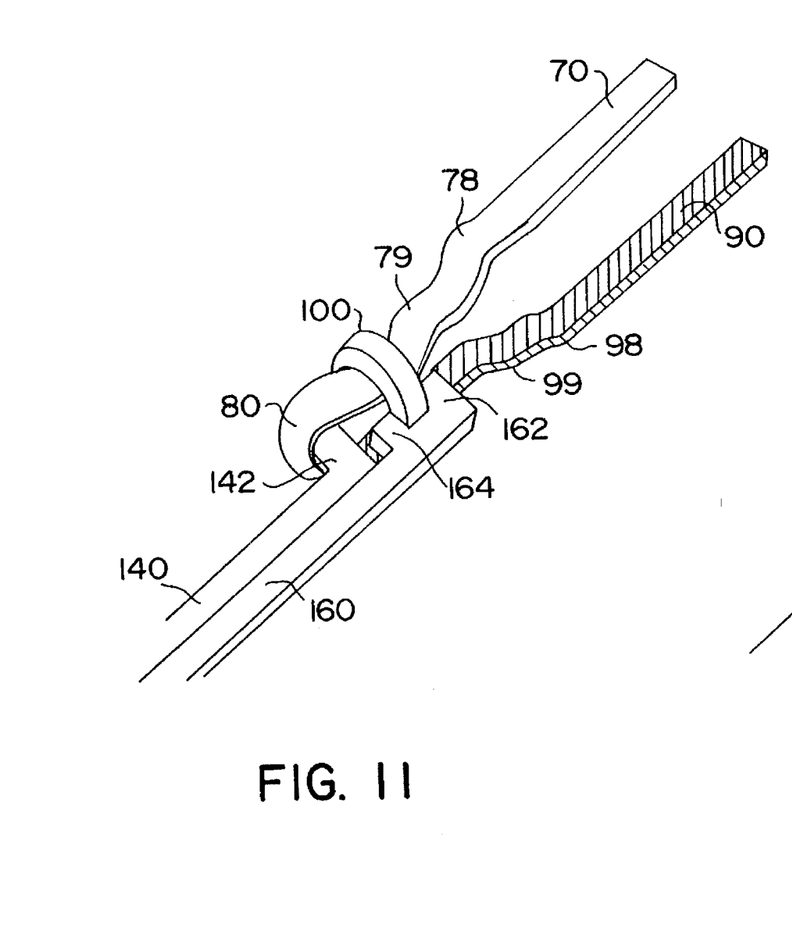
FIG. 11 shows the applicator engaging the bend and rigid ring of the open aneurysm clip according to the present invention.

Aneurysm clip 50 of the present invention is applied by the neurosurgeon using the aneurysm clip system (including cantilever spring 60, rigid ring 100, and applicator 120) of the present invention in the following manner. FIG. 11 shows the two legs 140 and 160 of applicator 120 positioned alongside open cantilever spring 60 and rigid ring 100 of aneurysm clip 50. Pin 142 on first leg 140 of applicator 120 is positioned in bend 80 of cantilever spring 60. Projections 162 and 164 on the end of second leg 160 engage rigid ring 100. Specifically, one projection 162 engages one face of rigid ring 100 while the other projection 164 engages the opposite face of rigid ring 100 with the body of rigid ring 100 occupying space 166 between perpendicular projections 162 and 164. Applicator 120 may be disposed inside a guide tube 200 to facilitate placement of applicator 120 (and cantilever spring 60 and rigid ring 100 held by applicator 120) at the site of the cerebral aneurysm.

Figure 12:
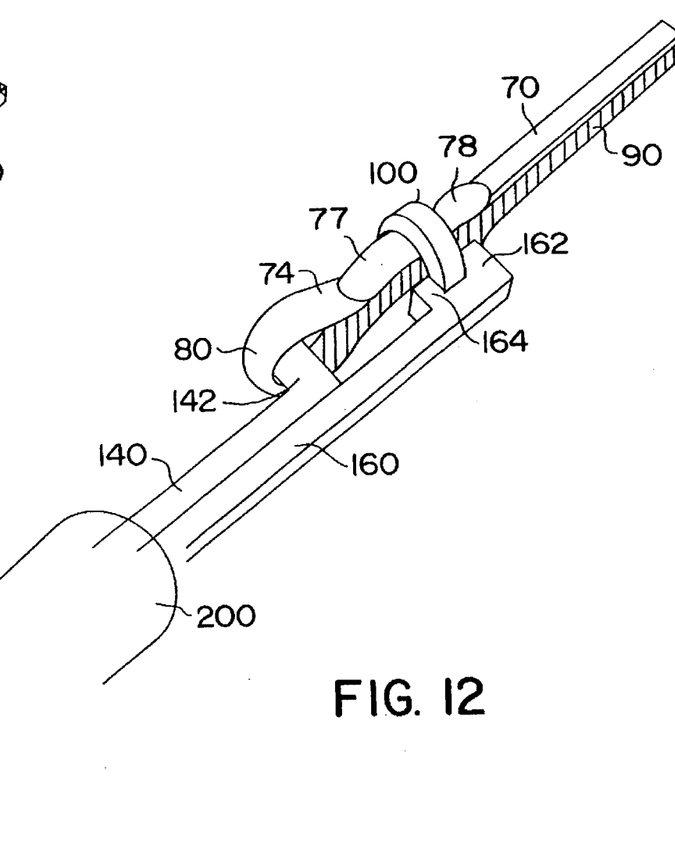
FIG. 12 shows the applicator engaging the bend and rigid ring of the closed aneurysm clip according to the present invention.

A scissoring or squeezing movement of blades 180 and 190 of handle 170 slides second leg 160 with respect to first leg 140. Pin 142 and first leg 140 keep cantilever spring 60 in a stationary position while projections 162 and 164 at the end of second leg 160 slide rigid ring 100 away from bend 80, over arms 70 and 90, into engagement with third bulges 79 and 99, and between the edges of first bulges 77, 97 and second bulges 78, 98 to close cantilever spring 60 as shown in FIG. 12. An opposite movement of blades 180 and 190 reverses the movement of rigid ring 100 and moves rigid ring 100 toward bend 80 and off arms 70 and 90 to open cantilever spring 60. FIG. 9 shows a typical "upward" shaft applicator 120. It should be noted that a "downward" shaft applicator would provide the reverse relative motion of second leg 160 with respect to first leg 140.

Thus, legs 140 and 160 of applicator 120 are in close sliding contact and move in response to scissoring or compression of handle 170. This sliding motion pushes rigid ring 100 in either direction, for opening or closing of arms 70 and 90. Pin 142 and projections 162 and 164 "hook" cantilever spring 60 and rigid ring 100. This "hook" creates an efficient method of applying or removing rigid ring 100 to or from cantilever spring 60. Applicator 120 also allows the user to manipulate aneurysm clip 50.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. An apparatus for clipping tissue during surgery on a cerebral aneurysm comprising:
    an aneurysm clip allowing visual control during application, providing a clipping force, and having:
        (a) a unitary, single-piece, integral cantilever spring open in the unbiased position, providing a spring force, and including (i) a first arm with a first end, a free end, an outer surface, and a first bulge positioned on said outer surface, (ii) a second arm with a first end, a free end, and an outer surface, and (iii) a bend disposed between said first end of said first arm and said first end of said second arm, and
        (b) a unitary, single-piece, integral rigid ring adapted to slip over and completely surround said first and second arms, retained by said bulge on said first arm, pressing said first and second arms together into a closed position against the spring force while preventing scissoring of said first and second arms; and
    an applicator allowing visual control during application of said aneurysm clip and having:
        (a) a first leg including a pin adapted to engage said bend of said cantilever spring of said aneurysm clip;
        (b) a second leg movable relative to said first leg and having means for engaging said rigid ring of said aneurysm clip and sliding said rigid ring on and off said first and second arms, said first and second legs positioned adjacent one side of said aneurysm clip rather than around said aneurysm clip thereby reducing visual obstruction; and
    means attached to said first leg and to said second leg for moving said second leg relative to said first leg.

2. An apparatus according to claim 1 wherein said first arm has a second bulge and a third bulge positioned on its outer surface and said second arm has a first bulge, a second bulge, and a third bulge positioned on its outer surface, said first bulges of said first and second arms preventing said rigid ring from sliding off said first and second arms in the direction of said bend, said second bulges of said first and second arms preventing said rigid ring from sliding off said first and second arms in the direction of said free ends of said first and second arms, and said third bulges of said first and second arms engaging said rigid ring and helping to maintain said rigid ring in position and to provide additional closing force by forcing said first and second arms of said cantilever spring together.

3. An apparatus according to claim 2 wherein said first arm has an angle disposed between its free end and its second bulge and said second arm has an angle disposed between its free end and its second bulge, said angles enhancing the clipping force of said aneurysm clip.

4. An apparatus according to claim 1 wherein said cantilever spring is a material selected from the group consisting of titanium, titanium alloys, ceramics, plastics, and composites and said material has a rigidity providing the clipping force of said aneurysm clip.

5. An apparatus according to claim 1 wherein said rigid ring is oval.

6. An apparatus according to claim 1 wherein the spring force provided by said cantilever spring is the only spring force of said aneurysm clip.

7. An apparatus according to claim 1 wherein said bend has a coil spring assuring return of said cantilever spring to its open, unbiased position upon removal of said rigid ring.

8. An apparatus according to claim 1 wherein the thickness of said cantilever spring is about 0.5 mm, the width of said bend of said cantilever spring is about 4.5 mm, and the length of said bend of said cantilever spring is about 4.0 mm, creating a volumetric visual obstruction of about 0.5×4.5× 4.0 mm.

9. An apparatus according to claim 8 wherein said rigid ring has a height of about 2 mm and a maximum outside diameter of about 5 mm.

10. An apparatus according to claim 1 wherein said pin is perpendicular to said first leg.

11. An apparatus according to claim 1 wherein said engaging and sliding means includes a pair of spaced projections perpendicular to said second leg, said projections engaging said rigid ring.

12. An apparatus according to claim 1 wherein said moving means includes a handle having a first blade and a second blade, said first blade attached to said first leg and said second blade attached to said second leg.

13. An aneurysm clip allowing visual control during application and providing a clipping force, said aneurysm clip comprising:
   a monolithic cantilever spring, produced without any machining operation requiring at least one of flow and removal of material, open in the unbiased position, providing a spring force, and having:
   (a) a first arm with a first end, a free end, an outer surface, and a first bulge positioned intermediate said first end and said free end on said outer surface,
   (b) a second arm with a first end, a free end, and an outer surface, and
   (c) a bend disposed between said first end of said first arm and said first end of said second arm; and
   a monolithic rigid ring adapted to slip over and completely surround said first and second arms, retained by said first bulge on said first arm, pressing said first and second arms together into a closed position against the spring force while preventing scissoring of said first and second arms.

14. An aneurysm clip according to claim 13 wherein said first arm has a second bulge and a third bulge positioned on its outer surface and said second arm has a first bulge, a second bulge, and a third bulge positioned on its outer surface, said first bulges of said first and second arms preventing said rigid ring from sliding off in the direction of said bend, said second bulges of said first and second arms preventing said rigid ring from sliding off said first and second arms in the direction of said free ends of said first and second arms, and said third bulges of said first and second arms engaging said rigid ring and helping to maintain said rigid ring in position and to provide additional closing force.

15. An aneurysm clip according to claim 14 wherein said first arm has an angle disposed between its free end and its second bulge and said second arm has an angle disposed between its free end and its second bulge, said angles enhancing the clipping force of said aneurysm clip.

16. An aneurysm clip according to claim 13 wherein said cantilever spring is a material selected from the group consisting of titanium, titanium alloys, ceramics, plastics, and composites and said material has a rigidity providing the clipping force of said aneurysm clip.

17. An aneurysm clip according to claim 13 wherein said rigid ring is oval.

18. An aneurysm clip according to claim 13 wherein the spring force provided by said cantilever spring is the only spring force of said aneurysm clip.

19. An aneurysm clip according to claim 13 wherein said bend has a coil spring assuring return of said cantilever spring to its open, unbiased position upon removal of said rigid ring.

20. An aneurysm clip according to claim 13 wherein the thickness of said cantilever spring is about 0.5 mm.

21. An aneurysm clip according to claim 20 wherein the width of said bend of said cantilever spring is about 4.5 mm and the length of said bend of said cantilever spring is about 4.0 mm, creating a volumetric visual obstruction of about 0.5×4.5×4.0 mm.

22. An aneurysm clip according to claim 21 wherein said rigid ring has a height of about 2 mm and a maximum outside diameter of about 5 mm.

23. An applicator allowing visual control during application of an aneurysm clip having (i) a cantilever spring open in the unbiased position including a pair of arms with a bend disposed between the arms and (ii) a ring pressing the first and second arms together into a closed position, said applicator comprising:
   a first leg having a pin adapted to engage the bend of the cantilever spring of the aneurysm clip;
   a second leg movable relative to said first leg and having means for engaging the ring of the aneurysm clip and sliding the ring on and off the first and second arms, said first and second legs positioned adjacent one side of the aneurysm clip rather than around the aneurysm clip thereby reducing visual obstruction; and
   means attached to said first leg and to said second leg for moving said second leg relative to said first leg.

24. An applicator according to claim 23 wherein said pin is perpendicular to said first leg.

25. An applicator according to claim 23 wherein said engaging and sliding means includes a pair of spaced projections perpendicular to said second leg, said projections engaging the ring.

26. An applicator according to claim 23 wherein said moving means includes a handle having a first blade and a second blade, said first blade attached to said first leg and said second blade attached to said second leg.

27. An applicator according to claim 26 wherein said first blade and said second blade move said second leg relative to said first leg in response to one of a scissoring and a squeezing force.

* * * * *